(12) United States Patent
Petric

(10) Patent No.: US 7,197,780 B2
(45) Date of Patent: Apr. 3, 2007

(54) UNIVERSAL HOSPITAL BED DESIGNED FOR NURSING THE IMMOBILE PATIENTS WITH ADDITIONAL BATHING EQUIPMENT

(76) Inventor: Dobrica Petric, Partizanska 43/28, 11000 Beograd, Serbia and Montenegro (YU)

( * ) Notice: Subject to any disclaimer, the term of this patent is extended or adjusted under 35 U.S.C. 154(b) by 100 days.

(21) Appl. No.: 10/508,654

(22) PCT Filed: Apr. 5, 2002

(86) PCT No.: PCT/YU02/00007

§ 371 (c)(1),
(2), (4) Date: Sep. 22, 2004

(87) PCT Pub. No.: WO03/082176

PCT Pub. Date: Oct. 9, 2003

(65) Prior Publication Data

US 2005/0144724 A1 Jul. 7, 2005

(30) Foreign Application Priority Data

Mar. 22, 2002 (YU) ................................. P-211/02

(51) Int. Cl.
*A61G 7/02* (2006.01)
*A61G 7/015* (2006.01)
(52) U.S. Cl. ..................... 5/604; 5/606; 5/616; 5/900
(58) Field of Classification Search ............... 5/600, 5/604, 606, 613, 616, 695, 900, 928, 722, 5/723, 727; 4/585, 587, 450, 451
See application file for complete search history.

(56) References Cited

U.S. PATENT DOCUMENTS

| 3,373,451 | A | * | 3/1968 | Schmidt | 4/585 |
|---|---|---|---|---|---|
| 5,168,587 | A | * | 12/1992 | Shutes | 5/81.1 T |
| 5,274,862 | A | * | 1/1994 | Palmer et al. | 5/81.1 R |
| 5,704,083 | A | * | 1/1998 | Nerg | 5/600 |
| 5,729,849 | A | * | 3/1998 | Garakani | 5/618 |
| 5,930,853 | A | * | 8/1999 | Akado | 4/547 |
| 6,006,378 | A | * | 12/1999 | Hayashi | 5/488 |
| 6,523,198 | B1 | * | 2/2003 | Temple | 5/604 |

* cited by examiner

Primary Examiner—Michael Trettel
(74) Attorney, Agent, or Firm—Sandra M. Parker, Esq.

(57) ABSTRACT

The universal hospital bed designed for nursing the immobile patients with additional bathing equipment" belongs to the category of the health equipment, intended for the health institutions, gerontology institutions and family households. The essence of the invention is in its constructive solution of the three-part bed, which using the mechanism for electrical and mechanical adjustment of the angles of the slope of the mobile parts of bed, could be converted into the form of (arm) chair. The belt holders and belts for fastening the patients are installed on the back part of the bed, and the antidecubitus mattress is placed along the whole bed, used as preventive protection of the patients against decubitus, or if patient already has it, for healing of the wounds. On the middle sitting part of the bed-mattress, part of the mattress is cut and the basic insert (41) is made of it, which if necessary, could be replaced with WC insert. Additional special equipment for bathing the immobile patients solves the problem of bathing the patients on the bed itself.

Figure 1:
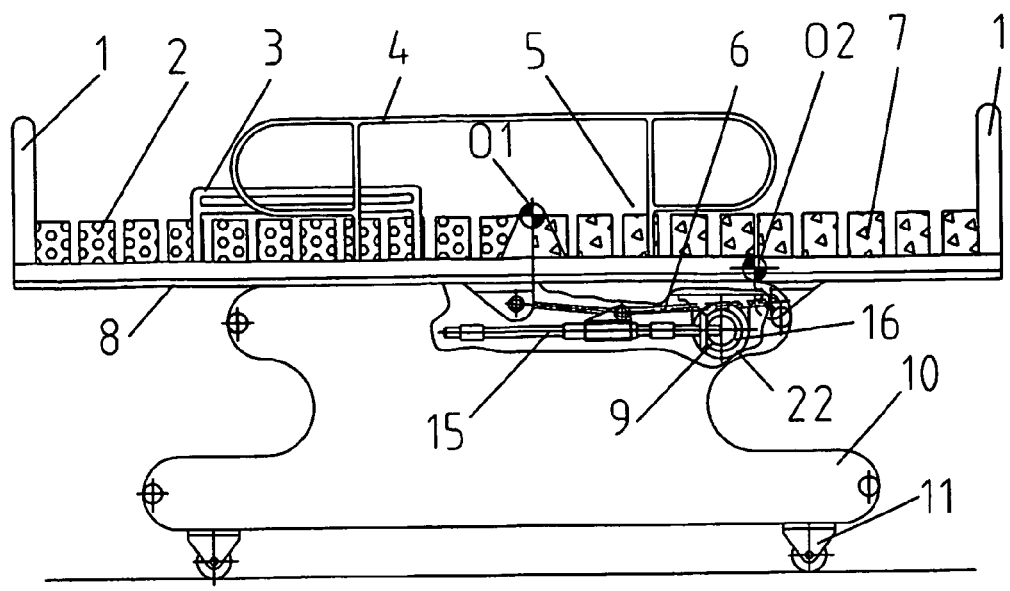

17 Claims, 7 Drawing Sheets b a

UNIVERSAL HOSPITAL BED DESIGNED FOR NURSING THE IMMOBILE PATIENTS WITH ADDITIONAL BATHING EQUIPMENT

RELATED APPLICATIONS

This application claims the foreign priority benefits under 35 USC 371 of PCT Patent Application, serial no. PCT/YU02/00007, filed on Apr. 5, 2002, published under serial number WO03082176 and Amended after EPO Search on Apr. 10, 2004, and parent application serial number YU20020000211/02 (P-211/02) filed on Mar. 22, 2002 in Serbia and Montenegro (former Yugoslavia), both with the same title and by the same inventor.

BACKGROUND OF THE INVENTION

1. Field of the Invention

The present invention relates to the field of health equipment.

2. Description of Related Art

The invention solves the problem of construction of the universal movable and easily articulated hospital bed for nursing the immobile patients while they are lying or eating, with the help of only one person, and most of all, for physiological purposes, regardless of age, sex and physical weight of the patient.

The invention solves the problem of the construction and installation of belts for fastening the immobile patients from transverse and longitudinal moving, while the patient is removed to the sitting position.

The invention solves the technical problem: the protection of the immobile patients against decubitus, using the constructive solution of antidecubitus mattress both in the process of prevention and in the process of treating decubitus.

The invention solves the problem of the construction of the middle (sitting) part of the bed used mainly for physiological purposes of the patients in their sitting position on the bed itself.

The invention solves the problem of construction and installation of the mechanism for electrical and mechanical adjustments of the angles of slope of the mobile parts of bed. Therefore bed could be converted into the form of (arm) chair for physiological purposes or some other useful actions, by adjusting the angles of slope of the mobile parts of the bed in the required position from zero to maximum inclination of the back part and part below the knees. The invention solves the problem of construction and installation of additional bed equipment, specially designed for bathing the immobile patients on the bed itself with only one person in charge.

The problem of nursing the immobile patients with nowadays solutions is familiar to all medical physicians who deal professionally with this kind of issue. We are talking about hard, often inhumane and unhygienic conditions for nursing the immobile patients which often includes more than one person involved in any form of patient care. The problem is far more complex if nursing is done in family circle.

The familiar constructional solutions of the hospital bed do not possess performances that above mentioned bed offers, for nursing the immobile patients from the aspect of simple, humane and above all functional service.

Analyzing the familiar solutions we can conclude that patients' extremities could be injured when we need to move them for no matter what purpose, especially when the patients are of heavy weight. The offered solution of hospital bed appreciably protects the patients against both physical, as well as psychological pressures of the personnel in charge of his care. This becomes apparent during long durational and several years lasting care of the immobile patients. Beside, the possible problems between patients and hospital personal are considerably reduced because of the conveniences of the offered constructional solution.

The invention, contrary to the beds that are nowadays used for the immobile patients, provides humane and high quality care of the immobile patients with only one person in charge.

The invention, contrary to the beds which are nowadays used for the immobile patients, provides preventive protection against decubitus using the antidecubitus mattress, in other words, rapid healing of decubitus.

The invention, contrary to the beds that are nowadays used for the immobile patients, solves the problem of bathing the patients on the bed itself using the additional equipment.

Using the mechanism for electrical or mechanical adjustment of the angles of slope of the mobile parts of bed you can convert it into the form of (arm) chair for physiological purposes or some other useful actions, or to be precise, you can adjust the angles of slope of the mobile parts of bed into the required position from zero to maximum inclination of the back part and the part below the knees, that is, there is a possibility to adjust only the back part of the bed into the required angle of slope, while the part bellow the knees remains in the horizontal position.

The special advantage of the above mentioned invention is also its universal usage for all other profiles of patients

SUMMARY OF THE INVENTION

The essence of the invention is presented in the constructive solution of the bed composed of three parts, which with the use of the mechanism for electrical and mechanical adjustment of the angles of slope of the mobile parts of bed, converts the bed to the form of (arm) chair.

The belt holders and the belts for fastening the patients from transverse and longitudinal moving are installed on the back part of the bed.

The construction of antidecubitus mattress provides the preventative protection of the patients against decubitus or if he already has it provides more effective healing of the wounds.

On the middle (sitting) part of the bed, a part of mattress is cut and "the basic insert" (42) is made of it. Using it in the normal conditions, namely in the cases when patients only lie, the above-mentioned hole is closed. For physiological purposes of the patients "The basic insert" is replaced with " WC insert" (51), but previously with the help of the fastening belts, the patient is fixed to the back part of the bed. Therefore, while bed is converted to the form of (arm) chair, any transverse and longitudinal moving is prevented.

Design of the equipment for bathing the immobile patients on the bed itself, as the additional special equipment of the bed, provides more humane treatment of the patients, especially in the cases when they are nursed at home in the family circle.

SHORT DESCRIPTION OF THE SKETCH FIGURES

FIG. 1: represents the side-view of the bed with its antidecubitus mattress composed of three parts.

Figure 2:
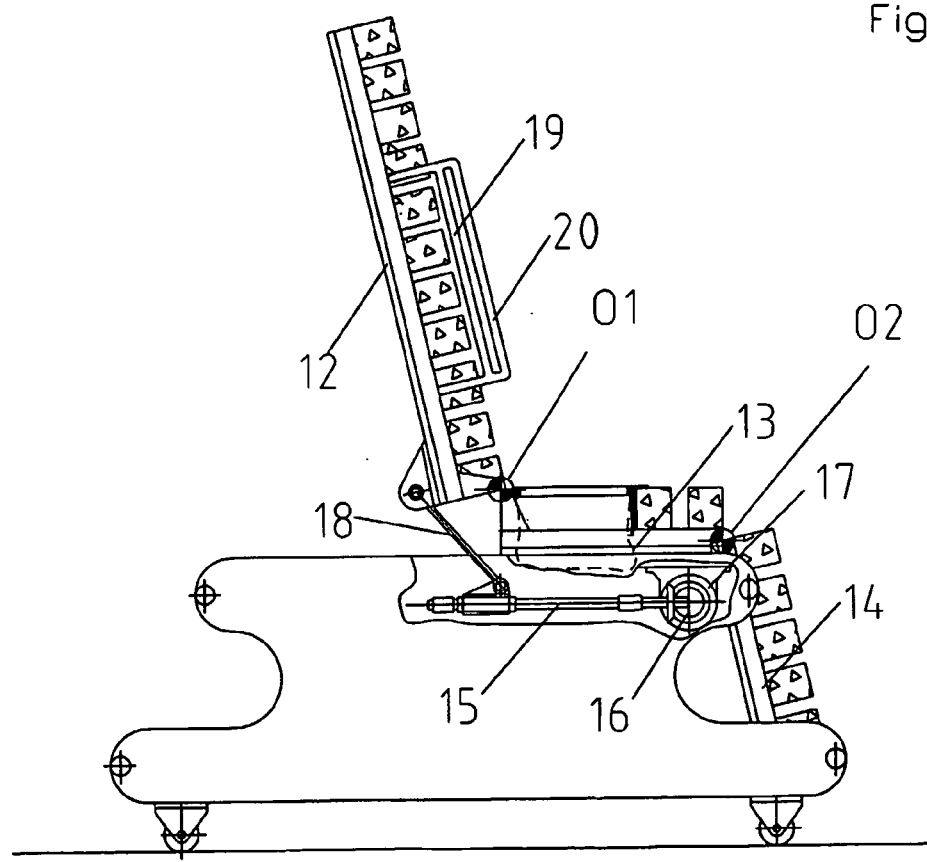

FIG. 2: represents the side-view of the bed in the form of (arm) chair.

Figure 3:
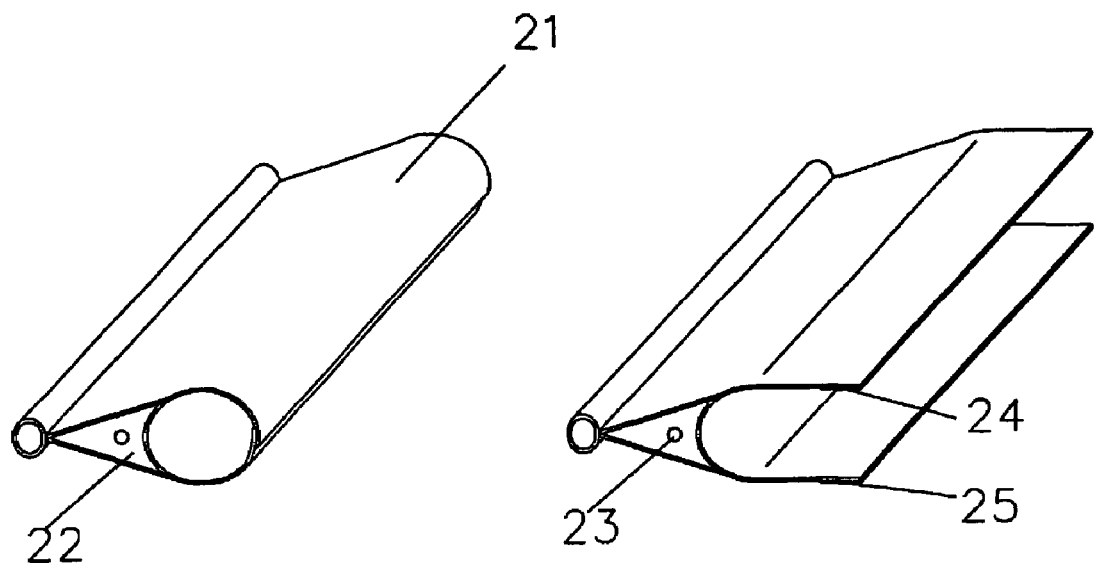
Figure 3:
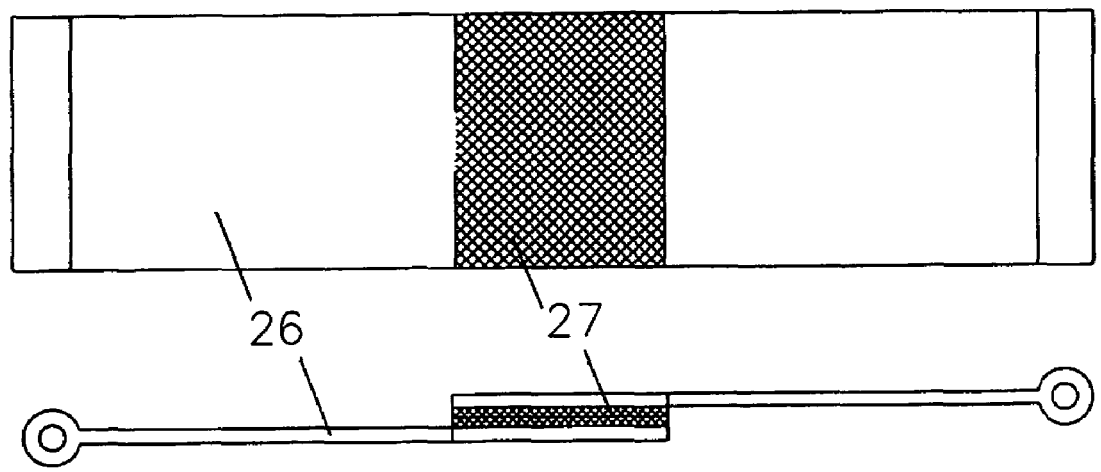

FIG. 3: represents the belts used for fastening patients.

Figure 4:
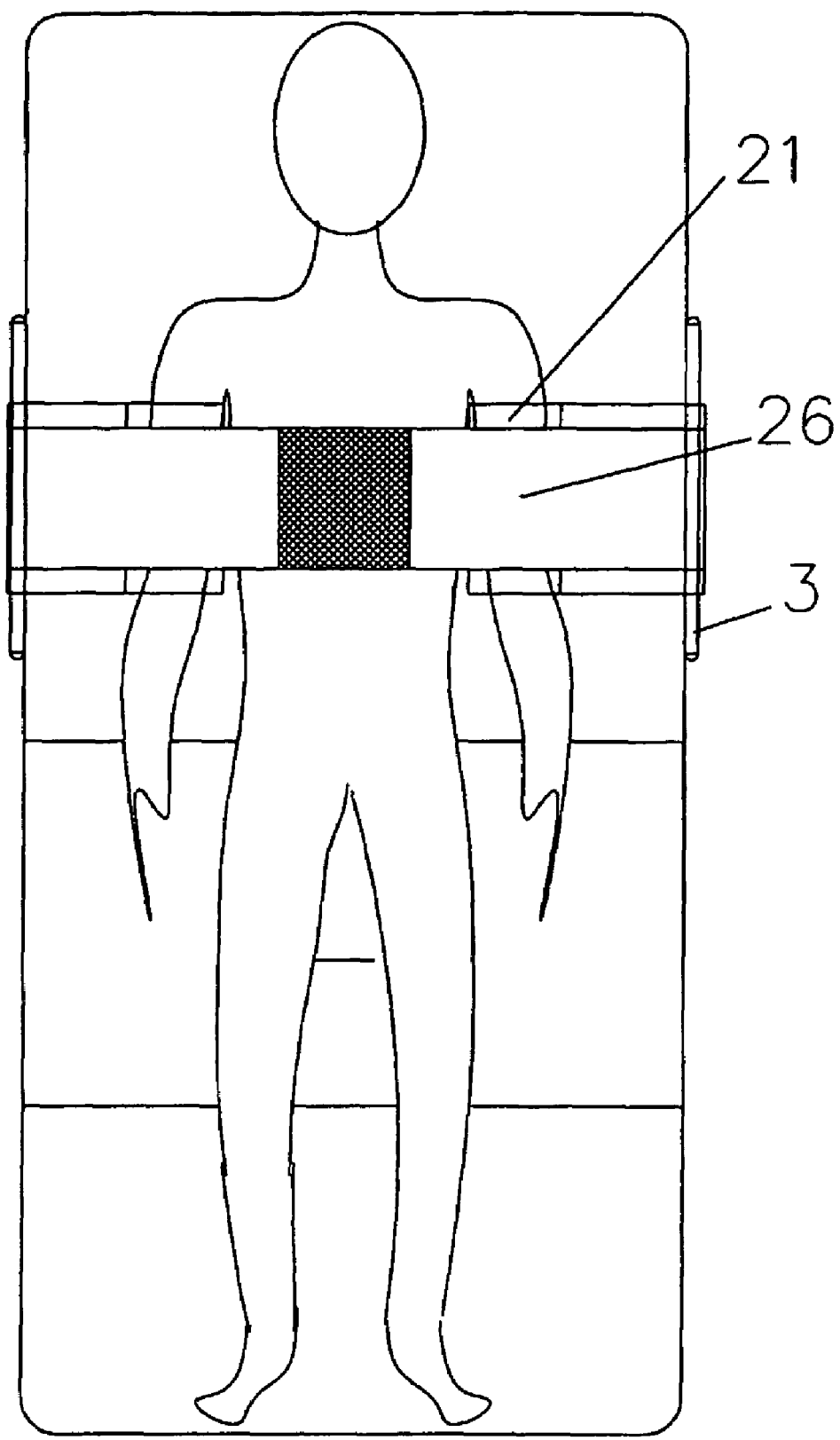

FIG. 4: represents the belts used for fastening patients to the bed against transverse and longitudinal moving in the ground-plan (before converting the bed in the form of (arm) chair).

Figure 5:
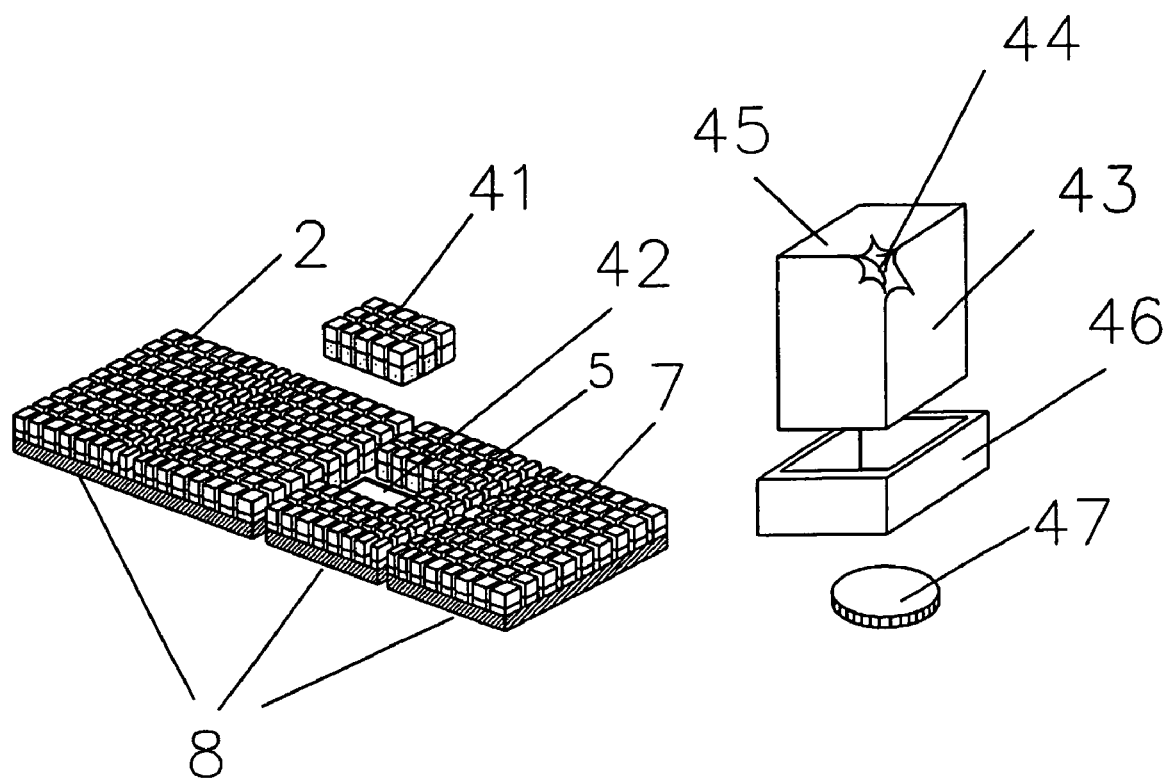

FIG. 5: represents the antidecubitus mattress made of little sponge cubes, polyurethane, and little cubes filled with air.

Figure 6:
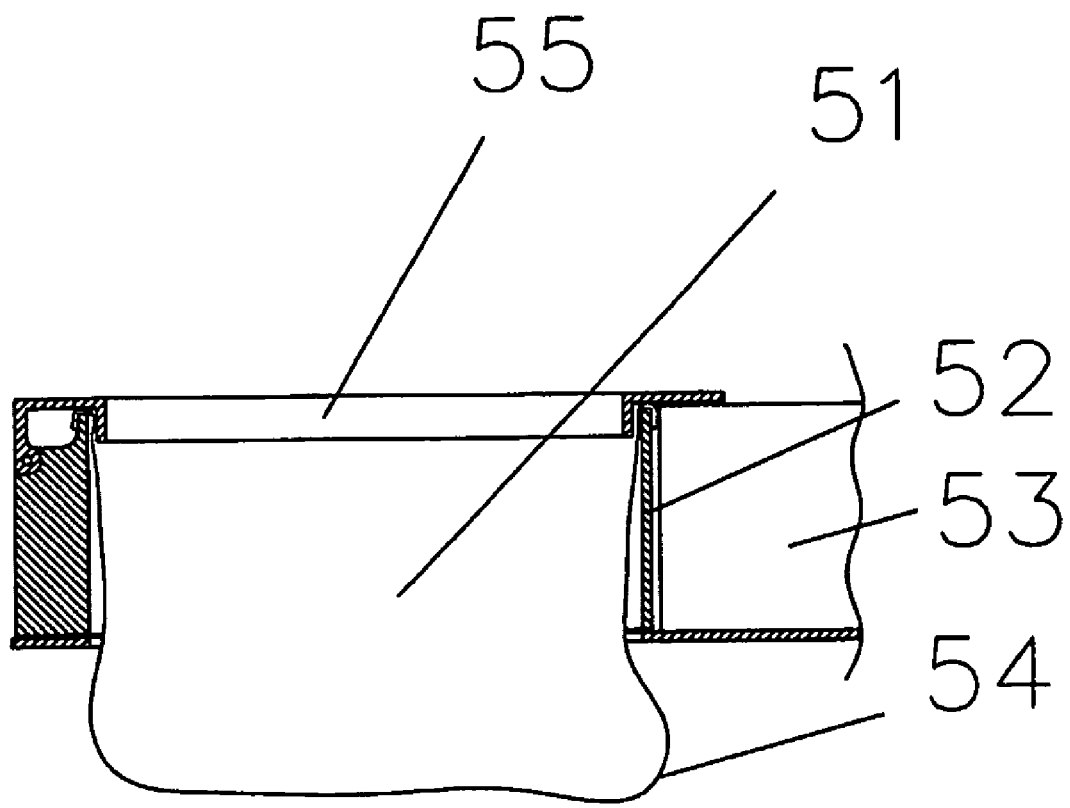
Figure 6:
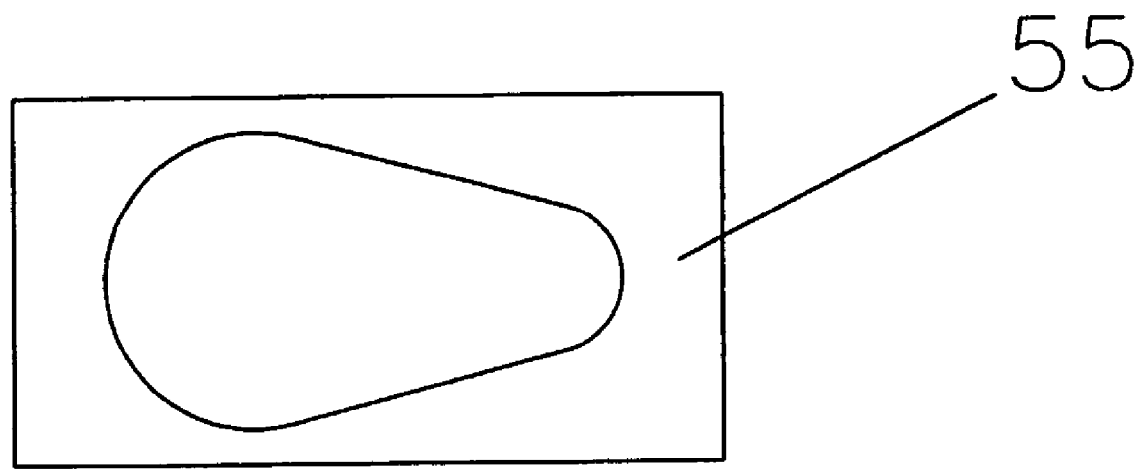

FIG. 6: represents "WC insert for single use only."

Figure 7:
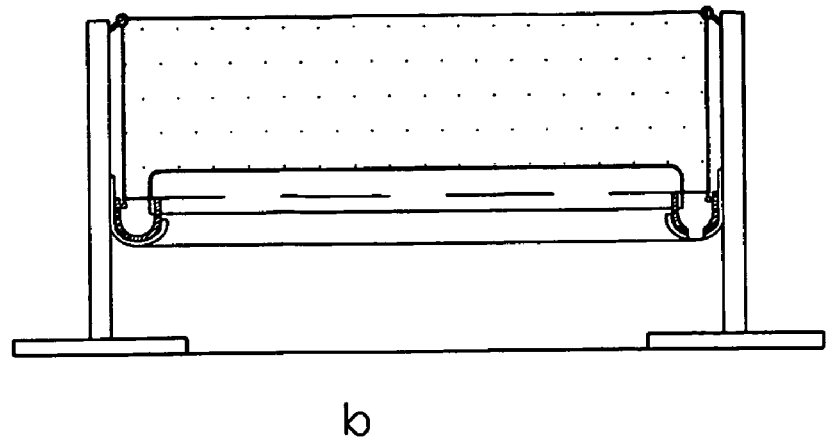
Figure 7:
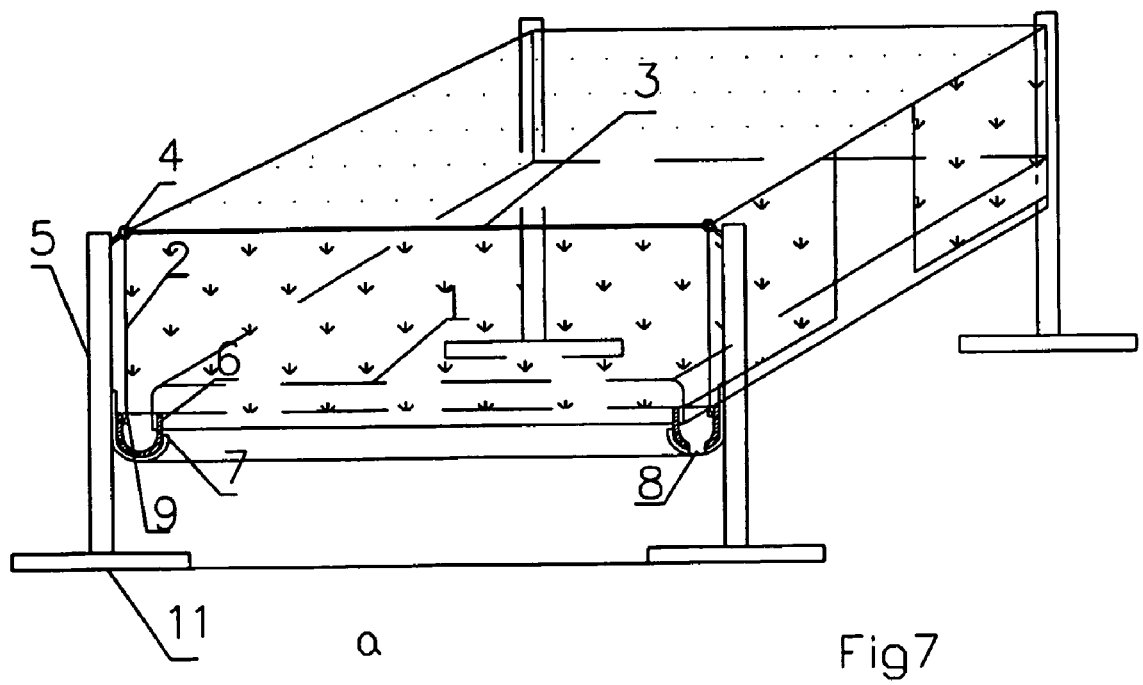
Figure 8:
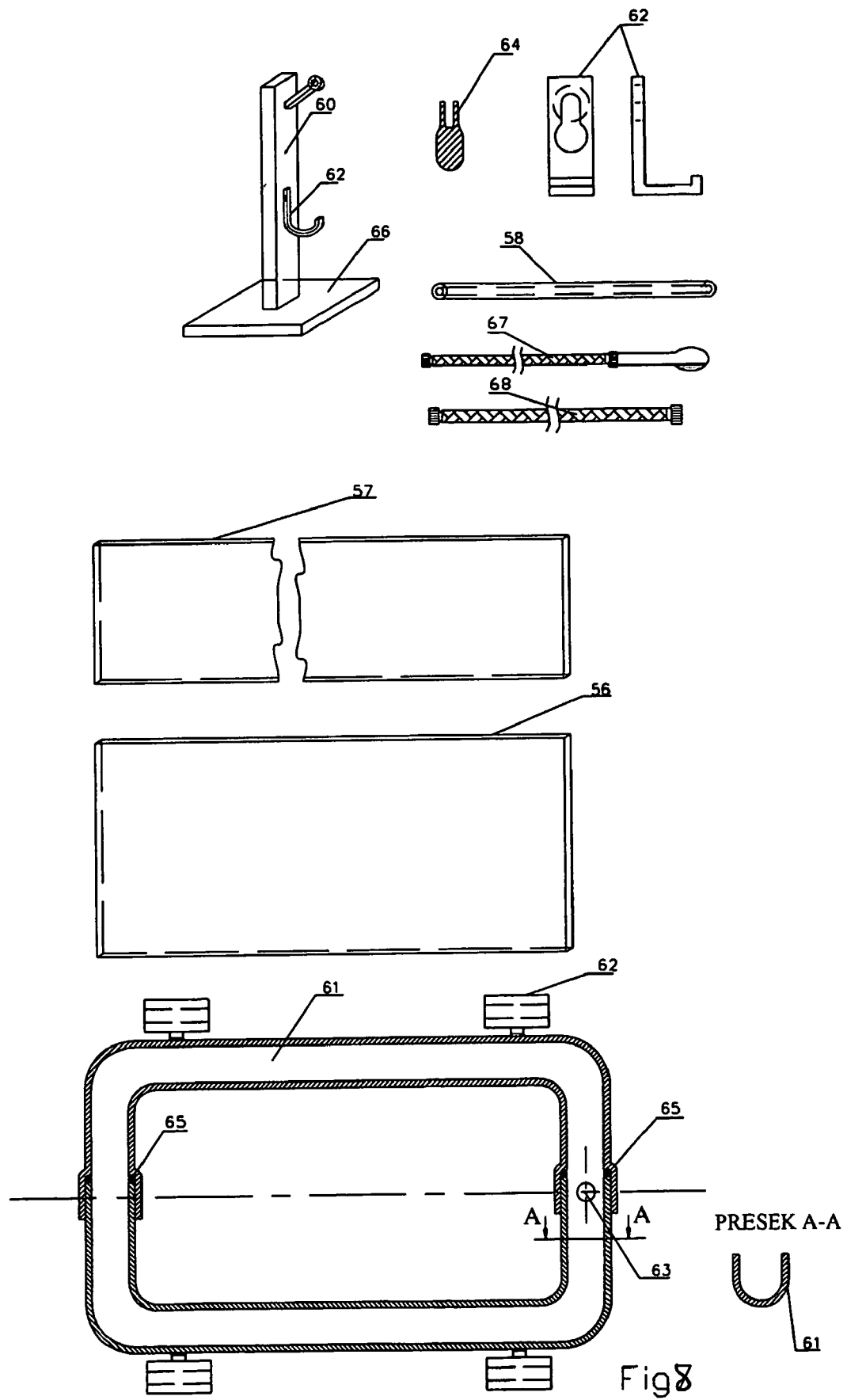

FIG. 7: represents the equipment for bathing the patients a) in the assembled state and b) in the cross-section FIG. 8: represents elements of bathing equipment.

DETAILED DESCRIPTION OF THE BED INVENTION

The figures represent constructional solution of the universal movable and easily converted hospital bed designed for nursing the immobile patients. It consists of bed support (10), wheels (11), mattress holder (8), mechanism for adjusting the angles of slope of the mobile parts of the bed (9) namely the back part (12) and the part below the knees (14), electromotor (17), reductor (22) with screw shaft (15), lever (18) for adjusting the angle of slope of the back part (12) of the bed and lever (6) for adjusting the part below the knees (14), axis of rotation of the mobile parts of bed (01) and (02) the back part of the mattress (2), middle part of the mattress (5) and below the knees part of the mattress (7), the front and back sides of bed (1) and lateral sides (4), with additional special equipment for bathing the patients which consists of: equipment holder (60), bed oilcloth (56), lateral oilcloth (57), holder (58) for lateral oilcloth, rings (59) for connecting the lateral oilcloth (57) and holder (58), trough (drain for the used water) (61), trough support (62), connection (63) of the water discharge hose, counterbalances (64) that are attached in a certain number to the edges of the oilcloth, O-ring (65) on the trough, supply hose (67) with the shower for hot and cold water and hose (68) for discharging the water from trough.

The middle part of the bed (13) is firmly attached to the bed support (10), while the back part (12) and the part below the knees (14) are mobile. On the middle part of the bed, as well as on the mattress (5) and mattress holder (8), the holes (42) for replacing "the basic insert" (41) with "WC insert" (51) are made, or just to say—the holes for plastic bags.

The holders of fastening belts (19 and 20) as well as the fastening belts (21 and 26), represented in FIG. 3, are used for fastening the patients to back part (12) of the bed in order to avoid any transverse moving of the patient. The belts (19) are air cushions which could be filled with air, if necessary, using a valve (23) and also attached to the hands of patients with the "burdock" band (24 and 25). The belt (26) is made of two wider strips with the "burdock" band (27) in the middle, used for fixing the patient to the bed.

If we want to convert the bed into the form of (arm) chair we need to activate the controls of mechanism (9) that at the same time raises the back part (12) and lowers the part below the knees (14). The applied mechanism represents one of familiar solutions used in practice.

For preventive protection of the immobile patients against decubitus—the antidecubitus mattress (FIG. 4) is constructed. This mattress consists of the following components: little cubes (43) made of sponge, polyurethane (44), or little cubes of plastic cloth filled with air. The cubes are covered with cloth (45) and put into the plastic box (46) for the impregnation On the bottom part of the plastic box the magnetic tape (47) or the "burdock" band is attached, and in the same way, metal cover or the "burdock" cloth is attached to the mattress holder (8).

For installing the "WC insert" (51) on the sitting part (13) of the bed first you need to remove "the basic insert (41)" and then replace it with "WC insert"(51). "WC insert" consists of: cylindrical holder (52) of plastic bag (54) for single use only, anatomically shaped lid (55) used for fixing the plastic bag, and also used as a sitting part for physiological purposes of the patients. The cylindrical holder (52) leans on the holder (8) of the middle mattress, while plastic bag (54) also partly goes through the hole of the holder (8) of the middle mattress.

For bathing the patients on the bed itself first you need to remove front and lateral sides of the bed and then to install the bathing equipment around the bed, (as it is shown on the FIG. 7), which consists of: four stands (66), holder of the lateral oilcloth (57), and trough (drain for the used water) (61), bed oilcloth (56), water discharge hose (68) and supply hose (67) with shower for hot and cold water.

The preparation procedure of bringing the patients into the sitting position for physiological purposes, which is at the same time the most complex part of nursing the immobile patients, is performed in the following order:

The patient has to be previously fasten with fastening belts (21 and 26) for the belt holder (3) or, in other words, for the back part (12) of the bed so that at the moment of converting the bed into the form of (arm) chair there would not be any unnecessary transverse or longitudinal moving of the patients (FIG. 2).

Raising the legs of patients with simultaneous removal of "the basic insert" (41) of the bed from the middle (sitting) part and installing the "WC insert" (51) instead, then taking legs down into the horizontal position.

Using the electrical and mechanical controls of the mechanism (9) adjust the angles of slope of the back (12) part of the bed and the part below the knees (14) so that the bed could be converted into the form of (arm) chair, and the patient into the sitting position, or, in other words, the natural position for physiological purposes.

When this is finished, now the procedure with bed and patient is in the vice versa direction to the previous one. Using the mechanism for adjusting the angles of slope of the mobile parts of bed (12 and 14), the bed is returned to the former horizontal position, the patient's legs are raised and hygienic cleaning is done. "WC insert" (51) is replaced with "the basic insert" (41), the fastening belts (21 and 26) are released from patient and therefore the patient is brought to the regular care treatment.

For bathing the immobile patient you need to install the above mentioned bed equipment exactly in accordance with the FIG. 7. Next, you need to adjust temperature of the water and then begin with bathing the patient. All the water used for bathing, passes between the oilcloths (56) and (57) into the trough (61) and then, through the water discharge hose (68) drains off into the plumbing fixtures of the building. When bathing is over, procedure goes on in the opposite direction; in other words, you need to turn off hot and cold water tap on the supply hose (67) with shower. Next, you need to remove the lateral oilcloth (57) as well as the oilcloth (56) placed under the patient. After this, separate the water discharge hose (68) from the trough (61). In the end you need to dismantle and remove the trough (61) from the stand (60). After the cleaning, all the above mentioned elements of the equipment are packed and put in the place for that purpose until the next use. Lateral sides (4) and front sides (1) of the bed are returned to their normal position.

For eating or preparing the patient for any kind of physical or intellectual work only the part, connected with fastening the patients and converting the bed into the form of (arm) chair with installation of the working board (as an integral part of the equipment), of the above mentioned procedure, is done.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A universal hospital bed transformable to an armchair, comprising:
    a supporting base;
    a sectional mattress holder having a sitting part attached to the supporting base and powered tiltable back and leg rests with independently adjusting slope angles; and
    a modular mattress having a plurality of removable mattress elements, independently and selectively detachable from the mattress holder for preventing bedsores; and
    at least one restraint belt removably connected to the mattress holder and having at least one air cushion and arm fastener.

2. The bed according to claim 1, wherein the mattress elements being made of material selected from the group comprising foam, sponge and air cushion.

3. The bed according to claim 1, wherein the mattress element being removably attachable to the mattress holder with a gripping aperture selected from the group comprising a fastening tape, loop-and-hook (burdock) fastener, magnetic fastener, snap and mattress element holder.

4. The bed according to claim 1, wherein the mattress and sitting part having corresponding openings enclosed with a removable mattress closure, the closure being removed for placement of a toilet seat and a replaceable waste bag.

5. The bed according to claim 1, wherein the back rest and leg rest having a powered slope adjustment equipment selected from the group comprising electrical, hydraulic, pneumatic and mechanical means.

6. The bed according to claim 1, further comprising a detachable bathing equipment protecting the mattress and having a frame placeable around the mattress, a water-impermeable mattress oilcloth, a water-impermeable lateral oilcloth including a draining hole, the lateral oilcloth being placeable over the mattress and the frame thereby forming a draining groove around the mattress, a water discharge hose being attachable to the draining hole and a water supply hose being attachable to a battery with hot and cold water.

7. The bed according to claim 1, wherein the mattress holder further comprising removable guardrails.

8. The bed according to claim 1, wherein the supporting base further comprising removable rollers.

9. A universal hospital bed transformable to an armchair, comprising:
    a supporting base;
    a sectional mattress holder having a sitting part attached to the supporting base and powered tiltable back and leg rests with independently adjusting slope angles;
    a modular mattress having a plurality of removable mattress elements, independently and selectively detachable from the mattress holder for preventing bedsores; and
    at least one restraint belt removably connected to the mattress holder, the restraint belt having at least one air cushion and arm fastener.

10. The bed according to claim 9, wherein the mattress elements being made of material selected from the group comprising foam, sponge and air cushion and wherein the mattress element being removably attachable to the mattress holder with a gripping aperture selected from the group comprising a fastening tape, loop-and-hook (burdock) fastener, magnetic fastener, snap and mattress element holder.

11. The bed according to claim 9, further comprising a detachable bathing equipment protecting the mattress and having a frame placeable around the mattress, a water-impermeable mattress oilcloth, a water-impermeable lateral oilcloth including a draining hole, the lateral oilcloth being placeable over the mattress and the frame thereby forming a draining groove around the mattress, a water discharge hose being attachable to the draining hole and a water supply hose being attachable to a battery with hot and cold water.

12. The bed according to claim 9, wherein the mattress and sitting part having corresponding openings enclosed with a removable mattress closure, the closure being removed for placement of a toilet seat and a replaceable waste bag.

13. The bed according to claim 9, wherein the back rest and leg rest having a powered slope adjustment equipment selected from the group comprising electrical, hydraulic, pneumatic and mechanical means, wherein the mattress holder further comprising removable guardrails and wherein the supporting base further comprising removable rollers.

14. A universal hospital bed transformable to an armchair, comprising:
    a supporting base;
    a sectional mattress holder having a sitting part attached to the supporting base and powered tiltable back and leg rests with independently adjusting slope angles, the back rest and leg rest having a powered slope adjustment equipment selected from the group comprising electrical, hydraulic, pneumatic and mechanical means;
    a modular mattress having a plurality of removable mattress elements, independently and selectively detachable from the mattress holder for preventing bedsores;
    at least one restraint belt removably connected to the mattress holder and having at least one air cushion and arm fastener; and
    a bathing equipment protecting the mattress;
    wherein the mattress holder further comprising removable guardrails and the supporting base further comprising removable rollers.

15. The bed according to claim 14, wherein the mattress elements being made of material selected from the group comprising foam, sponge and air cushion and being removably attachable to the mattress holder with a gripping aperture selected from the group comprising a fastening tape, loop-and-hook (burdock) fastener, magnetic fastener, snap and mattress element holder.

16. The bed according to claim 14, wherein the bathing equipment having a frame placeable around the mattress, a water-impermeable mattress oilcloth, a water-impermeable lateral oilcloth including a draining hole, the lateral oilcloth being placeable over the mattress and the frame thereby forming a draining groove around the mattress, a water discharge hose being attachable to the draining hole and a water supply hose being attachable to a battery with hot and cold water.

17. The bed according to claim 14, wherein the mattress and sitting part having corresponding openings enclosed with a removable mattress closure, the closure being removed for placement of a toilet seat and a replaceable waste bag.

* * * * *